United States Patent
Einecke et al.

(10) Patent No.: US 9,454,703 B2
(45) Date of Patent: Sep. 27, 2016

(54) METHOD, SYSTEM, IMAGING DEVICE, MOVABLE DEVICE AND PROGRAM PRODUCT FOR DETECTING STATIC ELEMENTS IN VIDEO AND IMAGE SOURCES

(71) Applicant: HONDA RESEARCH INSTITUTE EUROPE GMBH, Offenbach/Main (DE)

(72) Inventors: Nils Einecke, Offenbach (DE); Jörg Deigmöller, Offenbach (DE)

(73) Assignee: HONDA RESEARCH INSTITUTE EUROPE GMBH, Offenbach/Main (DE)

( * ) Notice: Subject to any disclaimer, the term of this patent is extended or adjusted under 35 U.S.C. 154(b) by 57 days.

(21) Appl. No.: 14/606,540

(22) Filed: Jan. 27, 2015

(65) Prior Publication Data

US 2015/0213318 A1    Jul. 30, 2015

(30) Foreign Application Priority Data

Jan. 28, 2014    (EP) ..................................... 14152834

(51) Int. Cl.
*G06K 9/00* (2006.01)
*G01N 21/94* (2006.01)
(Continued)

(52) U.S. Cl.
CPC ........... *G06K 9/00791* (2013.01); *G01N 21/94* (2013.01); *G01N 21/958* (2013.01);
(Continued)

(58) Field of Classification Search
USPC ........................................................ 382/103
See application file for complete search history.

(56) References Cited

U.S. PATENT DOCUMENTS

| 6,861,636 B2 | 3/2005 | Ockerse et al. |
| 7,636,114 B2 | 12/2009 | Aoyama |

(Continued)

FOREIGN PATENT DOCUMENTS

| DE | 10 2007 057 745 A1 | 6/2009 |
| EP | 1 983 334 B1 | 12/2009 |

(Continued)

OTHER PUBLICATIONS

European Search Report dated Jul. 10, 2014 corresponding to European Patent Application No. 14152834.9.

(Continued)

*Primary Examiner* — John Strege
(74) *Attorney, Agent, or Firm* — Squire Patton Boggs (US) LLP

(57) ABSTRACT

The invention relates to a method for determining a static element in images captured by an imaging means mounted on a movable device. The method comprises steps of acquiring a first image and a second image captured by the imaging means. The first image and the second image are captured at capture times separated by a time difference and the method is characterized by the time difference being selected depending on motion parameters of the movable device. A determination measure for corresponding regions of the first and the second image for representing a similarity of the corresponding regions is calculated and a static element of the first and the second image is determined based on the calculated determination measure. An output signal comprising information on the determined static element is generated.

22 Claims, 3 Drawing Sheets

(51) Int. Cl.
  *G01N 21/958* (2006.01)
  *G06T 7/20* (2006.01)
  *H04N 5/217* (2011.01)
  *G06K 9/52* (2006.01)
  *B60S 1/08* (2006.01)

(52) U.S. Cl.
  CPC .............. *G06K 9/52* (2013.01); *G06T 7/2006* (2013.01); *G06T 7/2013* (2013.01); *G06T 7/2053* (2013.01); *H04N 5/2171* (2013.01); *B60S 1/0818* (2013.01); *G06T 2207/10016* (2013.01); *G06T 2207/30252* (2013.01)

(56) References Cited

U.S. PATENT DOCUMENTS

| | | | |
|---|---|---|---|
| 2003/0169902 A1 | 9/2003 | Satoh | |
| 2007/0159551 A1* | 7/2007 | Kotani | H04N 1/4097 348/349 |
| 2007/0261711 A1* | 11/2007 | Fagrenius | G02B 27/0006 134/6 |
| 2007/0267993 A1* | 11/2007 | Leleve | B60S 1/0822 318/483 |
| 2009/0207245 A1 | 8/2009 | Hayashi et al. | |
| 2010/0215218 A1* | 8/2010 | Takahashi | H04N 7/185 382/104 |
| 2011/0080494 A1* | 4/2011 | Mori | H04N 5/2171 348/222.1 |
| 2013/0190965 A1 | 7/2013 | Einecke et al. | |
| 2014/0074292 A1* | 3/2014 | Sawada | B25J 19/023 700/259 |
| 2014/0232869 A1* | 8/2014 | May | H04N 5/2171 348/148 |
| 2015/0104064 A1* | 4/2015 | Guissin | G08G 3/02 382/103 |
| 2015/0339535 A1* | 11/2015 | Utagawa | H04N 5/225 348/118 |

FOREIGN PATENT DOCUMENTS

| | | |
|---|---|---|
| EP | 2 620 250 A1 | 7/2013 |
| JP | 2004-153422 A | 5/2004 |
| JP | 2008-160635 A | 7/2008 |
| JP | 2009-175121 A | 8/2009 |
| JP | 2013-153413 A | 8/2013 |
| WO | WO 2013/037403 A1 | 3/2013 |

OTHER PUBLICATIONS

Ramin Zabih et al., "Non-parametric Local Transforms for Computing Visual Correspondence," In Proceedings of European Conference on Computer Vision, Stockholm, Sweden, May 1994, pp. 151-158.

\* cited by examiner

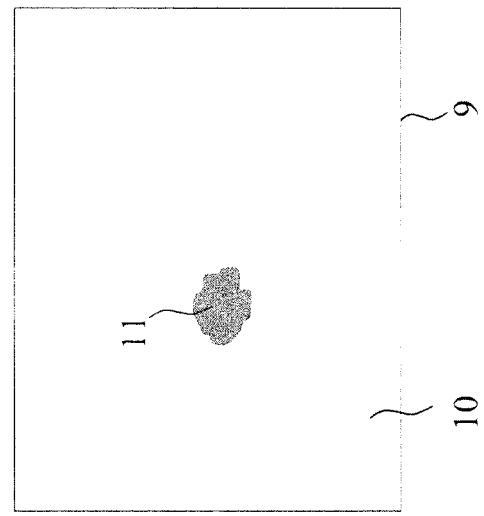
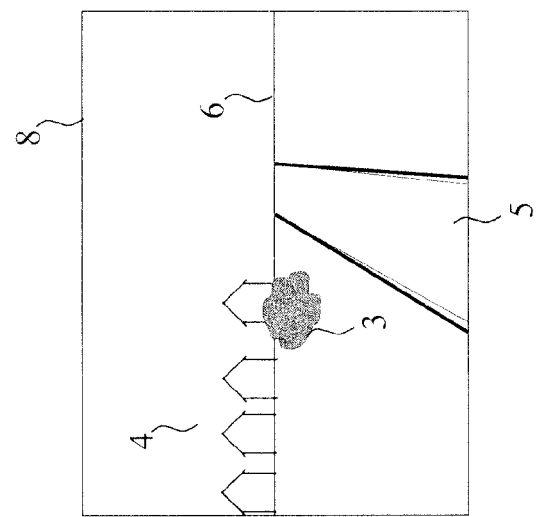
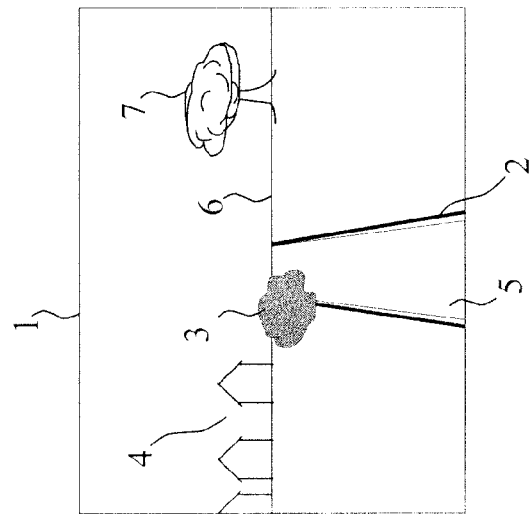

METHOD, SYSTEM, IMAGING DEVICE, MOVABLE DEVICE AND PROGRAM PRODUCT FOR DETECTING STATIC ELEMENTS IN VIDEO AND IMAGE SOURCES

BACKGROUND

1. Field

The invention relates to a method for determining static elements in image sources, a corresponding system, imaging device, a movable device comprising such an imaging device and a corresponding computer program product. In particular the analysis of images relates to detecting static flaws in images out of a sequence of images captured by an imaging means. The method is preferably used in vehicles that are equipped with driver assistance systems taking advantage of image processing, or autonomous vehicles.

2. Description of Related Art

The invention is in the field of autonomous devices relying on computer generated vision or other sensing techniques perceiving the surrounding of a vehicle on which such a system is mounted. An example for an autonomous device for applying the invention is an autonomous lawn mower but the invention is by no means limited thereto. In order to act autonomously with high reliability it is important that these autonomous devices perceive their surrounding with a certain detail under all circumstances. Imaging means such as cameras are increasingly employed in this area and provide capabilities to the autonomous devices related to human abilities such as distance estimation, street lane detection or complex object and people detection. Nevertheless it is of utmost importance to the overall system reliability that optical sensors such as cameras provide their image signals even under adverse conditions encountered in outdoor applications. Optical sensors and in particular their lenses become dirty or a lens of an optical sensor might receive scratches. Accordingly regular maintenance or cleaning the sensors becomes increasingly important. Hence it is also important to provide for autonomous movable devices to perform self-checks on optical sensors in order to generate information for suitable measures to counter the problem of reduced vision of the sensors and thus to avoid false analysis of the captured image.

The term "autonomous movable device" is commonly known in the art as referring to an unmanned device which has a drive means or propulsion means in order to move the autonomous device ("self-propelled device"), an onboard energy reservoir to power the propulsion means, one or more sensors and a control means functionally connected to the sensor(s) and the drive means. The autonomous device navigates in a free manner without human support based on sensor data acquired by the sensor(s) and processed in the control means in order to generate control signals for the propulsion means.

In the future for improving the functionality of autonomously operating movable devices particularly in outdoor environment more sensors and/or sensors with improved characteristics or altogether new capabilities such as optical sensors to the autonomous device have to be expected. However the quality of signals generated by these new sensors and in particular by optical sensors, e.g. cameras, depends on clean, lenses and transparent covers in the line of vision for acquiring visual information in a demanding outdoor environment. An outdoor environment, such as a garden under varying weather conditions, and performing tasks, such as cutting grass in case of an autonomous lawn mower, further increases the exposure of the sensor to dirt, sand, parts of plants, water, etc. Hence regular maintenance of the sensors is of high importance to avoid failure of the autonomous device due to sensor failure or faulty analysis.

The invention is particularly advantageous, when the sensor means comprises one or more optical sensors such as cameras. The use of cameras in the outdoor environment provides the autonomous movable device with an enhanced control capability, but the vision of cameras on the other hand significantly decreases with the dirt on a lens of a camera. Hence navigation and other operational characteristics of the autonomous robot device exposed to dirt profits from timely sensor cleaning.

The autonomous movable device of a preferred embodiment of the present invention is an autonomous lawn mower. The autonomous lawn mower also comprises working means including one or more blades for cutting grass and tends to soil rapidly with the cut grass adhering to any surface of the autonomous lawn mower when operating.

European Patent document EP1 983 334 B1 addresses the problem of detecting dust on a frontal lens of an optical system such as a surveillance camera. Additional optics generate sub-images in such a manner that the light rays generating these sub-images pass different positions in the front lens. The proposal in EP1 983 334 B1 needs additional technical means for detecting dust and flaw and is therefore complex and expensive to implement.

Patent document U.S. Pat. No. 6,861,636 B2 discloses a stereo camera setup to detect moisture on the surface of sensor arrays, e.g. for controlling wipers for a windshield of a vehicle. However two image sensors are required in order to generate stereoscopic depth and therefore introduce additional hardware and hence complexity into the sensor system for detecting moisture on the windshield.

US Patent document U.S. Pat. No. 7,636,114 B2 shows how to detect a pixel position corresponding to dust on the surface on an imaging sensor and its optical system. A special test setup is used to capture an image with uniform luminance. Then the intensity of each pixel is compared to a threshold which defines an expected intensity for the given uniform luminance. As uniform luminance is hardly found in a natural environment, the particular test setup is essential to the disclosed method and the method therefore ill suited to supervising a lens of a sensor during normal operation of a vehicle or autonomous movable device.

Patent application publication DE 10 2007 057 745 A1 discloses a process for controlling the wipers for a windshield of a vehicle by detecting objects on the windscreen. Objects on the windscreen are distinguished from objects in the background by capturing two images at different times and comparing the two images with each other. In the described embodiment the acquired images are transformed into edge images and for the purpose of comparison are multiplied pixel-wise in order to enhance objects such as dirt on the windscreen present in both images. If there are objects detected on the windscreen, a spray unit is activated for cleaning the windscreen. In the embodiment the single first edge image is analyzed for raindrops based on the specific structure of raindrops and the control of the wiper assembly is started based on the analysis result of the first image.

Parameters for generating edge images heavily depend on light intensity of the pixels. These parameters are complex in a diverse and rapidly changing light condition such as encountered by vehicles moving in real world environment and especially during night, or for autonomous lawn mowers operating in gardens or autonomous cleaning robots operating indoors. Further a vehicle employing the system according DE 10 2007 057 745 A1 might stand at red traffic lights, or cruise on a straight road with wide view over far distance. Given these circumstances, static objects on the windshield will be difficult to distinguish from the background which is also static under these conditions and the static object detection provide only results of limited reliability.

Taking the state of the art into consideration, the technical problem of determining the presence of static elements on the lens of an image or video source needs to be addressed overcoming the abovementioned disadvantages of the state of the art.

SUMMARY

The problem is solved by the method for determining a static element in images captured by an imaging means mounted on a movable device according to the claim 1. A movable device may be any device which performs a motion relative to its environment, in particular a vehicle or an arm of a robot. The method comprises a first step of acquiring a first image and a second image captured by the imaging means. According to the invention, the first image and the second image are captured at capture times separated by a time difference. The capture time of the first image and the capture time of the second image depend on motion parameters of the moving device. A motion parameter is any parameter that allows describing motion of the movable device relative to its environment. In a next step a determination measure for corresponding regions of the first and the second image is calculated. Corresponding regions are regions in the first and second image with identical position within the image and same shape. The determination measure represents a degree of similarity of the corresponding regions of the first image and the second image. Then in the next step a static element of the first and the second image is determined on the basis in the calculated determination measure. When the static element is determined, an output signal comprising information on the determined static element is generated.

Acquiring a first image and a second image selected for their specific capturing times provides the advantage that a first image and a second image can be chosen at optimised capture times for showing a low degree of similarity for objects of the environment depicted in the images and hence provide a particularly well suited occasion for determining static elements such as flaw. A basis for determining optimised capturing times of the first image and the second image is derivable from motion parameters of the imaging device. By selection of the capture times of the images the starting point in time for the determination of flaws and/or the time difference between the capture times can be dynamically adopted to the movement status of the movable device.

In a preferred embodiment the claimed method acquires images with a specifically adapted time difference $\Delta t$ between the capture times of the first image and the second image. If the imaging means is configured to capture an image stream with a frame rate, two successive images (frames) may be to close in time. There may be elements in the two consecutive images which are characterized by a high degree of similarity but which are nevertheless not caused by flaw or artifacts in the image but real time environment in which the camera is only slowly moved. Hence, taking motion parameters of the movable device on which the imaging means is mounted into account, enables to always calculate the determination measure on a suitable image pair and therefore efficiently use the limited calculation capacity on board of the movable device and to provide reliable results on quality of the captured images.

In a particularly preferred embodiment of the claimed invention, the determination measure is calculated in corresponding regions (patches) each of the first and the at least one second image for each pixel.

In a preferred embodiment the determination measure is calculated as a normalized determination measure. In particular, the determination measure can be determined as a correlation between corresponding regions of the first and the second image.

In an embodiment of the method for the determination of the static element an element in the first image and the second image is determined for which the calculated determination measure exceeds a threshold.

In one embodiment the determination measure is one of a normalized cross correlation (NCC), a summed normalized cross correlation (SNCC), a summed or squared difference measure for rank transformed images and a summed hamming distance of census transformed images.

Contrary to the state of the art comparing pixels based on a luminance intensity and calculating a intensity difference for determining a similarity of pixels corresponding to a small difference in luminance intensity, the inventive correlation-based approach to determine similarity based on normalized pixel values shows stable and reliable results even under conditions of changing light whereas purely intensity-based similarity metrics yield instable results. Such metrics are not able to cope with varying light conditions. If for example a vehicle moves from a region exposed to bright sunshine into a shadowed area, the inventive correlation based determination measure based on correlation will still show a reliable result contrary to the state of the art intensity-based approach.

In an alternate embodiment calculating the determination measure is based on calculating optical flows between the first image and the second image. When the determination measure is based on optical flows, a static element in the first and the second images is determined by determining for which regions the optical flow is smaller than a predefined (second) threshold or for which the optical flow is zero or almost zero.

The inventive method is advantageously employed when the imaging means is configured to capture a sequence of images. The imaging means in this embodiment can be a video camera capturing a video comprising a plurality of time sequential images ("frames") at a given frame rate.

In a particular embodiment a plurality of determination measures are calculated for a plurality of different pairs of images selected from the sequence of images. The pairs of images differ from each other in that at least one of the images is different. The first and the second image are selected from a sequence of images generated by the imaging device, whereas a time difference between successive image frames of the sequence of images differs from the selected time difference between the capture time of the first and the capture time of second image. The time difference between successive image frames of the sequence of images corresponds to an inverse of the frame rate for capturing the image frames.

In a further embodiment an average determination measure for determining the static element of the first and second images is calculated from the plurality of calculated determination measures calculated from the sequence of images.

In an embodiment a determination measure is calculated by pixel-wise correlation of respective patches of the first and the second image from the first and the second image comprising a plurality of pixels each.

In a preferred embodiment of the method, the motion parameters of the imaging means correspond to drive parameters of the moving device, the drive parameters comprising at least one of a vehicle speed and a turning angle of the vehicle.

In an embodiment of the method the first and the second image are selected from a sequence of images the image capturing times of which fall in a time period during which a turning motion of the imaging means and/or the moving device mounting the imaging means is performed.

In an embodiment the method for determining a static object is started when a turning motion of the imaging means and/or the moving device on which the imaging means is mounted is recognized.

In another embodiment the method comprises a step of determining underexposed and/or overexposed areas in the first and the second image. When underexposed and/or overexposed areas are determined the underexposed and/or overexposed areas in the first and the second image are excluded from determining static elements of the first image and the second image.

In another embodiment of the method a number of detected static elements is determined and when the number of static elements exceeds a third threshold, the output signal comprising information about the determined static elements is generated. The output signal may then form the basis for any measures taken in response to the determined static elements or trigger those countermeasures such as reporting a sensor failure, maintenance requirement or cleaning requirement of the imaging means (sensor). Particularly the output signal initiates performing a lens-cleaning procedure and/or reporting to a user of a detected imaging means state and/or stopping moving the device and/or moving the device mounting the imaging means to a cleaning position or to a base station. The number of static elements is preferably calculated as number within an area of predetermined size in the image.

The number of determined static elements of the first and second image may correspond to a number of determined static pixels of the first and second image.

The inventive method is advantageously used in an image processing system configured to perform the method steps as discussed before. The method for determining static elements can be implemented in form of a computer program product performing the method and configured to be run on a computer or on a digital signal processor. The method may be advantageously employed in an imaging device, for example a camera comprising the image processing system.

The invention can in particular be implemented in an image processing module, which can be part of a car, a motorbike, or any other vehicle. The invention is particularly suited to be applied in real-world environments, such as encountered when driving a car or in any kind of autonomously operating device or vehicle.

The movable device may be one of an automobile device, an autonomous robot device, an autonomous lawn mower, a land mobile vehicle, a car, a motor cycle, a manned or an unmanned aerial vehicle, a sea vehicle, an orbital vehicle, a spacecraft.

A further advantageous embodiment of the invention provides in the output signal information on the determined static elements as flaw on the imaging means to the control means for using the information in order to control a cleaning procedure of an autonomous movable device for the cleaning of the imaging means. Hence the imaging means may be cleaned in a more targeted manner by providing information where dirt affects the vision in the aperture of the imaging means or the cleaning procedure may be performed until a predefined vision quality is achieved.

BRIEF DESCRIPTION OF THE DRAWINGS

The method for image analysis and the respective method are in their general and specific details explained now with reference to the appended figures in which
FIG. 1A shows a first image taken by an imaging device
FIG. 1B shows a second image taken by an imaging device,
FIG. 1C depicts a correlation map generated in an embodiment of the method.

DETAILED DESCRIPTION

Figure 2:
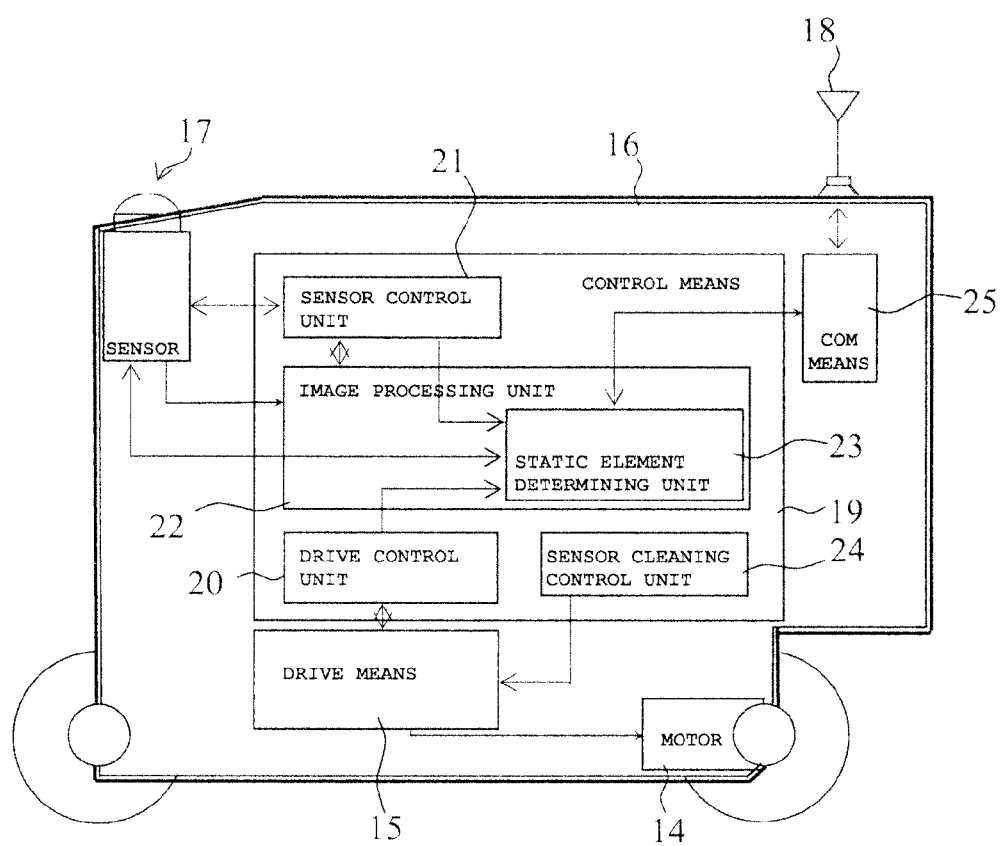
FIG. 2 shows an embodiment of a vehicle on which an imaging means is mounted and which includes means for detecting static elements in a sequences of images taken by the imaging means.

The following description and explanation refers to an autonomous vehicle such as a lawn mower as a typical example of a moving device according to the invention. Of course it is evident that any details which are discussed in the following section may also be used in conjunction with other (autonomous) vehicles or any (autonomous) robot device employing imaging means as sensors.

In particular the moving device may be one of a cleaning robot, a vacuum cleaner or even any self-propelled (e.g. electrically propelled) vehicle. The moving device may also be an industrial robot device, e.g. an automatically controlled manipulator programmable in three or more axes, e.g. used on a manufacturing site and employing an imaging means as sensor.

The imaging means or sensor as referred to in the present description may be any optical apparatus adapted to capture images, e.g. by means of an optical assembly such as a lens system, and store the images or relay the images to another unit. The images captured by the imaging means may be still images that may be part of moving images such as movies. The imaging means may operate on light in the visible spectrum or in other ranges such as infrared. The imaging means may be camera, a camera module, a video camera, a LIDAR sensor etc. For the purpose of the present invention it is to be noted that a single imaging means is to be understood when using the term imaging means, although a moving device or vehicle according to the invention may of course include multiple imaging means for implementing stereo vision by providing depth perception additionally.

The quality of the single image depends on many factors and one of those factors affecting the image quality adversely may be summarized under the term "flaw". Flaw within this patent application (or artifact) describes the effect of dirt on an imaging lens or a transparent cover in front of the lens in the imaged area of an imaging device, scratches, glass cracks, rain drops, insects or foliage, etc. on a windscreen. Depending on the application of the imaging means, the detection of flaws requires a decision whether to proceed with an ongoing action as the flaws are assumed to be not critical to system performance, or to take appropriate measures such as cleaning an imaging means where deemed necessary or even stopping execution of an assigned task and going into a safe state (e.g. safety stop of a vehicle) and/or reporting to a user about the determined situation.

FIG. 1A shows a first image 1 taken by an imaging device, wherein a lens or a transparent lens cover of the imaging device is soiled with dirt in an area 3 in the first image 1 characterized by a dark spot. The first image 1 is captured ("taken") by the imaging device at a first time t1 and depicts a scene with a village represented by a group of houses 4 in a left portion of the first image, a road 5 between road markings 2 and leading to a horizon line 6 in a central portion and a single tree 7 near the horizon line 6 in a right portion of the first image 1.

The imaging device is turned to the left after the capture time $t_1$ and at a time $t_2=t_1+\Delta t$ a second image 8 is captured by the imaging device.

The time difference $\Delta t$ is a difference between the capture time t1 of the first image and the capture time $t_2$ of the second image.

FIG. 1B depicts the second image 8 captured at the time $t_2$ after a time difference $\Delta t$ has elapsed starting from $t_1$. Due to the yaw motion of the imaging device, objects in the second image 8, e.g. the village 4 and the road 5, appear at different positions in the second image 8 compared to the first image 1 or even vanish from the scene due to the changed line of vision and depicted area e.g. the tree 7.

The yaw angle is an angle that describes a turning or rotating motion of a device, e.g. the imaging device around a vertical axis.

However the lens or a transparent lens cover of the imaging device 2 soiled with dirt still comprises the area 3 in the second image 8 as a dark spot at an unchanged position. The area 3 corresponding to a flaw on the lens of the imaging device is visible at exactly the same position in the first image 1 as well as in the second image 8 and thus forms a static element in the image 1 and 2.

The basic idea of the claimed invention is to detect such static elements 3 (or areas in the first image 1 and the second image 8) as indicators for flaws or artefacts. According to the invention the first image 1 and the second image 8 are correlated and the result of such a correlation is represented by FIG. 1C in the form of a correlation map 9.

FIG. 1C shows the result of a pixel-wise correlation between the pixels of the first image 1 and the second image 8 shown in FIGS. 1A and 1B. The grey scale of the areas in FIG. 1C represents a strength of correlation between the respective information in first image 1 and the second image 8. In FIG. 1C "White" refers to a low correlation value and "Black" represents a high correlation between images 1 and 8. Due to the axis of vision of the imaging device, executing a turning motion to the left between time $t_1$ and time $t_2$ all elements of the scene in the first image 1 move to the right in the second image 8. Hence every scene element such as village 4, tree 7 or road 5 will be shown with low correlation value in the correlation map 9, as the corresponding elements of the first image 1 and the second image 8 show different scene elements.

On the other hand the flaw on the lens of the imaging device moves commonly with the line of vision of the imaging device and therefore is situated at a corresponding position in the first image 2 and the second image 8. The dark region is determined to be a static element in the first image 1 and the second image 8. The correlation map 9 accordingly comprises an area of high correlation 11 at the respective position depicted in black. Thus the correlation map 9 shows the position of the flaw on the lens of the imaging device as an area of high correlation.

An advantageous approach for calculating correlations between images is to use block-matching or patch-matching. In order to perform block-matching an image patch or block representing an element of the image around one pixel of the image is extracted and compared with a corresponding image patch of another image.

For detecting artifacts a patch around one pixel in the first image 1 is correlated with a patch around the same pixel in the second image 8. If the image elements show the same element the determination measure calculated will have a high correlation value otherwise the calculated determination measure will show a low correlation value. This procedure can be repeated for each pixel and its patch to generate the correlation map.

Contrary to the state of the art comparing pixels based on a luminance intensity and calculating an intensity difference for determining a similarity of pixels (corresponding to a small difference in luminance intensity), the inventive correlation based approach on determining similarity shows stable and reliable results even under conditions of changing light whereas intensity based similarity metrics yield instable results due to not being able to cope with varying light conditions. If for example a vehicle with a camera mounted thereon moves from a region exposed to bright sunshine into a shadowed area, the inventive correlation based determination measure based on correlation will show reliable results far superior to the state of the art intensity-based approach.

The determination measure according to the claimed invention applies in an embodiment the normalized cross correlation (NCC). In a further embodiment the determination measure is based on the summed normalized cross correlation (SNCC).

The NCC is determined for a corresponding image patch in the first images I1 1 and the second image I2 8 according to equation (1)

$$\rho_i = \frac{\sum_{x \in X(i)} I1_x I2_x - \mu_{I1}^i \mu_{I2}^i}{\sigma_{I1}^i \sigma_{I2}^i}, \qquad (1)$$

wherein $\mu_{I1} \mu_{I2}$ are patch mean values, $\sigma_{I1} \sigma_{I2}$ are the patch variances for the corresponding patch in the images I1 and I2, X(i) is a set of all pixels within a patch at a position i, $I1_x$ and $I2_x$ are pixel x in the respective image I1 or I2, $\rho_i$ is the cross correlation between an image patches of I1 and I2.

The SNCC is determined for a corresponding image patch in the first images I1 1 and the second image I2 8 according to equation (2)

$$\overline{\rho}_i = \Sigma_{x \in X(i)} \rho_x, \qquad (2)$$

wherein in equation (2) $\overline{\rho}_i$ is the summed average of cross-correlation values inside a region, X(i) is a set of all pixels within a patch at a position i, $\rho_i$ is the cross correlation between an image patch of I1 and I2.

Other correlation measures such as the summed difference of rank transformed images (RT) or the summed hamming distance of census transformed image may also employed in further embodiments of the invention as determination measures. For purpose of applying the respective procedures to the inventive method of determining static elements in the first image 1 and the second image 8, reference is made to the Ramin Zabih and John Woodfill: "Non parametric local transforms for computing visual correspondence" (in: proceedings of European Conference on computer vision, Stockholm, Sweden, May 1994, pages 151-158), whose contents are herein incorporated by reference.

FIG. 2 depicts an autonomous device 12 according to an embodiment with its functional units.

An imaging means 17 is arranged near the front end of the main body 16 in the main movement direction of the autonomous device 12 and extends with its lens beyond the housing 16 (main body) of the autonomous device 12 for an advantageous field of vision. The autonomous device 12 in this embodiment may be an autonomous lawn mower 12. The imaging means 17 can be protected by a transparent sensor cover in order to protect the lens from mechanical damage by plants, thorns, other obstacles, weather phenomena like rain, etc and which is not shown in FIG. 2. The imaging means 17 of an embodiment is an optical sensor and acquires visual image data of the environment of the autonomous lawn mower 12 and provides the acquired image data in an image signal to a control means 19 of the autonomous lawn mower 12.

The shown autonomous device 12 comprises in addition to the at least one imaging means 17 (camera) and the control means 19, a drive means 15. An image processing unit 22 is configured to process the image signal received from the imaging means 17. A static element determining unit 23 included in the control means 19 and the image processing unit 22 is specifically adapted to detect static elements as presumed flaw affecting the images acquired by the imaging means 17 by executing the inventive method for determining static elements.

The control means 19 receives from the driving means 15 the drive parameters of the autonomous vehicle 12. The drive parameters include at least one of a movement speed and a turning angle of the autonomous vehicle and may also comprise both and/or further parameters.

The static element determining unit 23 is configured to generate an output signal for initiating a suitable measure when determining static elements in the first image 1 and the second image 8 and thereby identifying flaw on the imaging means 17 or a transparent cover over the imaging means 17. The output signal can, for example in one embodiment be adapted to start a sensor cleaning procedure under control of the sensor cleaning control unit 24 include in the control means 19.

The output signal can, for example in an embodiment initiate displaying a warning symbol on a dashboard including a display means when the vehicle is a car, a motorcycle or other manned vehicle or aircraft, etc. A warning symbol display may also be triggered by the output signal at a remote control station of a remotely piloted vehicle or a display on a base station of an autonomous lawn mower 12. The output signal for initiating and/or controlling countermeasures may also prompt the transmission of a message to a user via a communication means 25 of the autonomous device 12 or to a sensor cleansing station, for example a sensor cleaning station integrated in a base station.

The communication means 25 may apply any wireless or optical (infrared) communication standard and be adapted to use an antenna 18 arranged on the main body 16 of the autonomous device 12 for communication to a communication counterpart. In particular the communication means may link the autonomous device 12 to wireless local area network (WLAN) or a mobile cellular network according to a communication standard such as GSM, UMTS, LTE and its variants and evolvements.

Figure 3:
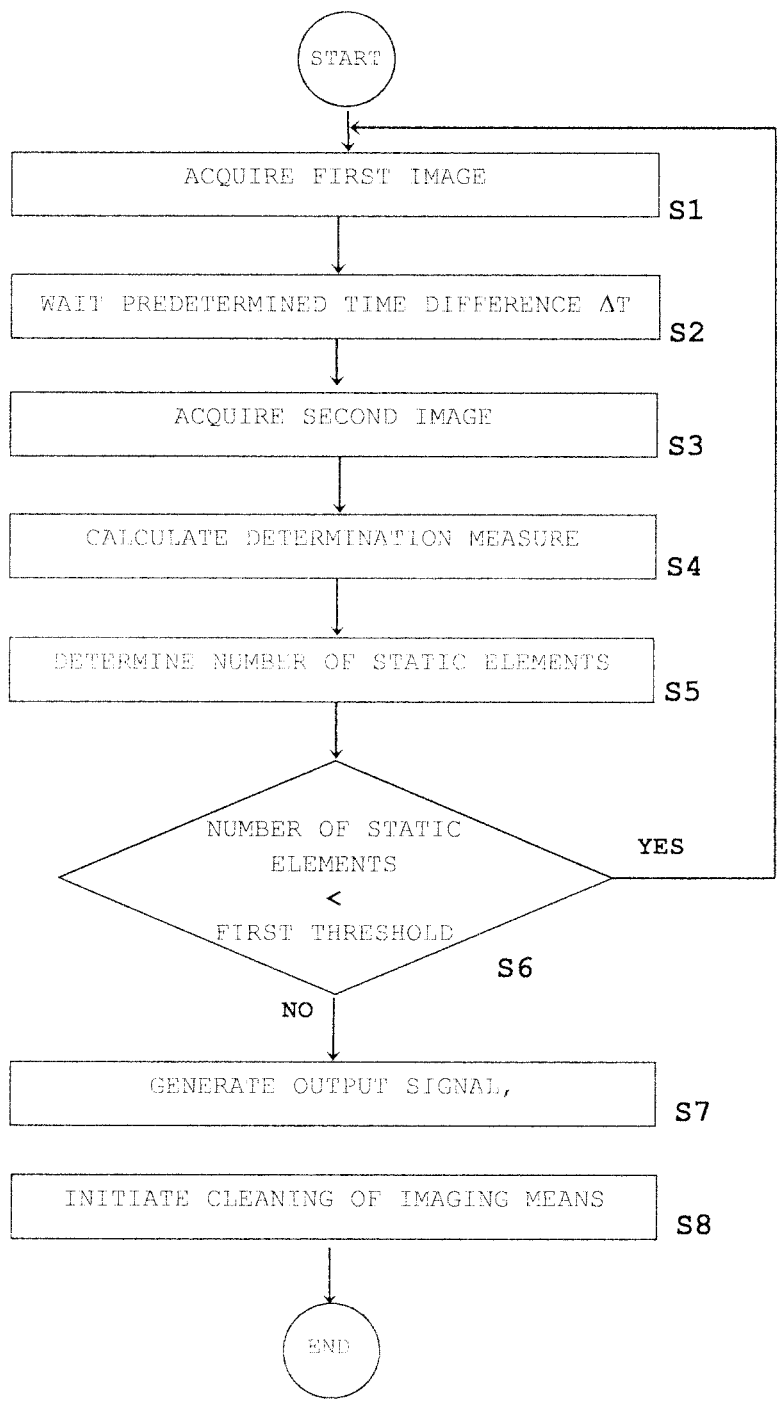
FIG. 3 is a flowchart depicting steps of a flaw detecting method in video and image sequences according to an embodiment of the invention.

FIG. 3 depicts a flowchart including steps of a method for determining static elements in video and image sequences according to an embodiment of the invention.

In step S1 a first image 1 is acquired by the flaw detecting unit 23. The first image 1 has been captured by the sensor means 17 within a sequence of images.

The capture time for acquiring the first image 1 may be selected when at least one motion parameter indicates a turning movement of the imaging means 17. The first image 1 may be acquired when at least one motion parameter exceeds a specific threshold for starting the method for detecting static elements 11. For example it is determined, that a rotary speed of the imaging device 17 exceeds a predefined threshold value (limit value) and therefore a suitable capturing time for a first image 1 and starting the method for determining static elements 11 is given.

In step S2 the static element determining unit 23 waits a predetermined time interval $\Delta t$ before proceeding to a next step S3. The length of the time interval $\Delta t$ depends on one or more motion parameters of the imaging means 17 or the autonomous vehicle 12. A drive parameter of the autonomous vehicle 12 is for example a movement speed or a turn angle (yaw angle) of the autonomous movable device 12.

The time interval $\Delta t$ may be chosen corresponding to a default time value when the method is started by acquiring the first image 1. The length of the time interval $\Delta t$ in one embodiment can be selected so that an increase in a motion parameter being a measure for the speed of motion results in a reduced time interval $\Delta t$. An increasing time interval $\Delta t$ may be set in case of a respective reduction in one or more motion parameters of the imaging means 17. The dependency of the time interval $\Delta t$ from the one or more motion parameters may be for example a linear or a nonlinear dependency. The time interval $\Delta t$ may be selected from a range of possible time intervals $\Delta t$ starting from a minimum time interval up to a maximum time interval. The time interval $\Delta t$ (or time difference $\Delta t$ between capturing times of the first image 1 and the second image 8) is in any case suitably selected for calculating the determination measure on an image pair comprising predominantly moving objects in the images in contrast to possible static elements 11 on the lens of the imaging means 17.

The motion parameter may be a rotational speed of a turning movement of the imaging device 17. For a specific rotational speed of the motion parameter a corresponding value for the time interval $\Delta t$ may be read from a table. For this purpose the table stored in the static element determining unit 23 links motion parameter values such as rotation speed, movement speed and/or turning angle with respective values for the time interval $\Delta t$. As an alternative suitable values for the time interval $\Delta t$ may be calculated according to a stored equation in the static element determining unit 23 from motion parameters each time the inventive method is started by acquiring a first image 1.

It is also possible to start acquiring the first image 1 at $t_1$ when on the basis of a motion parameter describing a turning movement (angle velocity) it can be recognized that a rotational movement is performed by the movable device. In such a case a predetermined time difference may be used for determining $t_2$.

In step S3 the static element determining unit 23 acquires a second image 8 from the sensor means 17.

The static element determining unit 23 then calculates the determination measure for the first image 1 and the second image 8 in a step S4. The calculation of the determination measure may be performed by pixel-wise correlation using a correlation metric such as summed normalized cross correlation (SNCC) or a similar metric. The result of the correlation in step S4 is used to generate a correlation map 9 according to FIG. 1C comprising a number of static elements. Static elements 11 are elements of the correlation map 9 showing a high value for the calculated correlation measure.

In step S5 succeeding to the calculation of the determination measure in step S4 the number of static elements 11 in the correlation map 9 or a part thereof is determined.

If in the succeeding step S6 the number of static elements 11 between the first image 1 and the second image 8 is found to be smaller than a second threshold, the flaw detecting method according to an embodiment of the invention and as executed by the static element determining unit 23 proceeds to step S1 and acquires another first image 1.

If in the in case in step S6 the determination measure is found to be equal or greater than the threshold, the static element determining unit 23 proceeds to a next step S7 and generates an appropriate output signal containing information that the imaging means 17 is adversely affected by flaw. The output signal may also comprise information where in the images 1, 8 static elements 11 are determined and how many static elements 11 are determined. The output signal is then used in the next step S8 to initiate suitable (counter) measures in order to cope with the stated problem for the imaging device 17. The appropriate measures taken may include at least one of the following actions, e.g. performing imaging means 17 cleaning under control of the sensor cleaning control unit 24, generating a respective error message and transmitting the message via the communication means 25 and antenna i8 to a base station of the autonomous movable device 12 or to a user device. In an embodiment of the invention the autonomous movable device 12 is an autonomous lawn mower 12 and operates from a base station and returns in regular intervals for recharging its batteries to the base station and a charging position in (or at) the base station. When the static element determining unit 23 determines static elements 11 in the images captured by the imaging device 17 of the autonomous movable device 12 in step S6, the autonomous movable device 12 accordingly returns to the base station and approaches a specific sensor cleaning station integrated with the base station.

While the method according to an embodiment of the invention is described with respect to FIG. 3 as determining static elements 11 from a first image 1 and a second image 8, the inventive method may be further detailed in yet another embodiment.

Determining static elements in order to determine flaws or artefacts from any two images by means of cross-correlation tends to provide results including noise. Hence in an embodiment of the invention the results of a great number of correlations are averaged in order to provide more stable results for the determination of static elements.

One approach of averaging a number of correlations comprises to acquire a plurality of frames or images out of a sequence of images or an image stream. Then a number of inter-frame cross-correlations are calculated for several pairs of images out of the acquired plurality of images. The calculated correlations of the plural image pairs are then averaged, e.g. by calculating mean measures in order to generate an averaged determination measure. Hence the effects of outliers are removed from or reduced in the calculation measure and accordingly the reliability of the static element determination is further improved.

A further preferred embodiment of the claimed method for determining static elements or flaws acquires images for calculating the determination measure with a specifically selected time distance $\Delta t$ between the capture times of the images. If the imaging means 17 is configured to acquire an image stream with a (frame) rate, two successive images (frames) may be to close together to distinguish static elements (flaws) from environmental objects. There may be elements in the two consecutive images which have a high degree of similarity but which are however not caused by flaw or artefacts in the image.

Examples where elements of the two consecutive images are at least almost identical but the high value of the correlation measure is not caused by static elements flaws might result from the vehicle being halted or only slowly moving. When the autonomous movable device 12 with the imaging means 17 is following a straight line of movement and in particular when in combination with an imaging means 17 having a narrow field of vision whose line of vision points into the line of movement of the autonomous movable device 12, two consecutive images out of a sequence of images captured at a high frame rate may only include almost static elements between the first image 1 and the second image 8 due to the perspective mapping of the 3-dimensional real world to the 2-dimensional image plane performed by the imaging means 17.

A similar effect is observed, when there are no prominent features in the field of vision of the imaging means 17. Particularly critical in this respect are for example clouds. Due to the large spatial distance of the clouds to the imaging means 17, the autonomous movable device 12 with the imaging means 17 needs to travel a great distance on a straight line in order to recognize a change between the depicted object in the first image 1 and the second image 8. By selecting the first image 1 and the second image 8 at times with a time difference $\Delta t$ and explicitly not immediately consecutive images separated by the inverse of the frame rate, the determination measure provides more favorable results. The time difference $\Delta t$ between capture times of the first image 1 and the second image 8 are in a specific embodiment of the inventive method selected from a range of 10 seconds to 60 seconds, preferably depending on the current speed of the movable device.

If the time difference $\Delta t$ is selected to long, some static elements 11 not entirely static but slow moving itself may not be reliably determined when executing the method. Static elements representing raindrops on a transparent sensor cover or on a windscreen behind which the imaging means 17 is mounted may move slowly in a vertical direction due to gravity or at least partially in horizontal direction due to a relative movement of the autonomous movable device 12 to the ambient air. Hence in a preferred embodiment of the invention drive parameters of an autonomous movable device 12 mounting the imaging means 17 are provided from the drive means 15 via a drive control unit 20 in the control means 19 to the static element determination unit 23. The static element determination unit 23 analyzes the received drive parameters and selects a first image 1 and a second image 8 with respect to the time interval $\Delta t$ between their capture times in order to constitute a suitable image pair for calculating the determination measure for static element determination.

The one or more imaging means 17 are usually mounted fixed on a vehicle 12 and the drive parameters of the vehicle correspond to motion parameters of the imaging means 17. This particularly applies to motor cycles, cars, autonomous lawn mowers or autonomous (vacuum) cleaners. However if the imaging means 17 is movably mounted onto the movable device 12, motion parameters characterizing a movement of the imaging means 17 and acquired by the sensor control unit 21 in the control means 19 are also provided to the static element determining unit 23. The static element determining unit 23 then analyzes the received motion parameters of the imaging means 17 and selects a first image 1 and a second image 8 with respect to the time difference Δt between the respective capture times of the first image 1 and the second image 8 in order to select a suitable image pair for calculating the determination measure for static element determination. The slower the device moves the longer Δt is selected.

In an embodiment of the invention the static element determining unit 23 selects the first image 1 and the second image 8 with respect to the drive parameters of the movable device 12 preferably with capture times for the images 1, 8 only during a time interval in which the autonomous movable device 12 executes a turning movement. A turning movement of the autonomous movable device 12 mounting imaging means 17 with a fixed line of vision in relation to the autonomous movable device 12 results in all objects in the scene captured in an image by the imaging means 17 moving into the opposite direction to the direction of the turning movement. Hence significant changes between the first image 1 and the second image 8 are caused by the turning movement of the autonomous movable device 12. Contrary thereto flaws or artefacts on the lens of the imaging means 17 or on a windshield in front of the imaging means 17 move with the autonomous movable device 12 and remain at the respective pixel position of the first image 1 and the second image 8. Hence first image 1 and second images 8 captured during a time when the autonomous movable device 12 is travelling along curves of a road or during turning movement at a intersection are preferably selected for achieving distinct correlation peaks for static element determination by the inventive static element determination method.

The static element determination unit 23 of an advantageous embodiment of the invention selects the first image 1 and the second image 8 with respect to the drive parameters of an autonomous movable device 12 preferably with capture times during the autonomous movable device 12 executing a turning movement. The autonomous movable device 12 in the form of an autonomous lawn mower 12 usually shows an exceptionally small turning radius due to their specific carriage layout. In case of a long time that has elapsed since the last static element determination was performed it is also possible to initiate a turning movement and at the same time start such determination process.

For the explanation of the structure of the invention and the details thereof, an autonomous movable device 12 was used. But the invention may also used for Advanced Driver Assistance System (ADAS). This is particularly evident, when the output signal comprising static element determination information is used to generate a control signal that informs a user of a possibly fatal failure in sensor state and reliability of generated sensor information. The invention is well suited to provide reliability information for the acquired image data acquired by any imaging means in any systems whose system performance is based on acquired image data under adverse conditions.

The invented claimed is:

1. Method for determining a static element in images captured by an imaging means mounted on a movable device, the method comprising steps of:
   acquiring a first image and a second image captured by the imaging means, wherein the first image and the second image are captured at capture times separated by a time difference,
   calculating a determination measure for corresponding regions of the first image and the second image for representing a similarity of the corresponding regions,
   determining a static element of the first image and the second image based on the calculated determination measure,
   generating an output signal comprising information on the determined static element, and wherein
   the capture times of the first image and the second image that are acquired depends on at least one motion parameter of the movable device.

2. The method according to claim 1, wherein
the time difference Δt is dependent on at least one motion parameter of the movable device.

3. The method according to claim 1, wherein
the determination measure is calculated on the corresponding regions each of the first image and the second image for each pixel.

4. The method according to claim 1, wherein
the determination measure is calculated as a normalized determination measure.

5. The method according to claim 1, wherein
the determination measure is one of a normalized cross correlation, a summed normalized cross correlation, summed or squared difference measure for rank transformed images and a summed hamming distance of census transformed images.

6. The method according to claim 4, wherein
for determining the static element an element in the first image and the second image is determined for which the calculated determination measure exceeds a threshold.

7. The method according to claim 1, wherein
the determination measure is based on calculated optical flows between the first image and the second image.

8. The method according to claim 7, wherein
for determining the static element an element in the first image and the second image is determined for which the optical flow is smaller than a second threshold or for which the optical flow is zero.

9. The method according to claim 1, wherein
the imaging means is configured to capture a sequence of images.

10. The method according to claim 9, wherein
the first image and the second image are selected from the sequence of images generated by the imaging device with a frame rate, and
that the frame rate differs from the time difference between the first image and the at least one second image.

11. The method according to claim 9, wherein
plural determination measures are calculated for a plurality of pairs of images of the sequence of images.

12. The method according to claim 11, wherein
an average determination measure for determining the static element is calculated from the calculated plural determination measures.

13. The method according to claim 1, wherein
the motion parameters of the imaging means correspond to drive parameters of the movable device, the drive parameters comprising at least one of a speed and a turning angle of the movable device.

14. The method according to claim 1, wherein
the first image and the second image are selected having the capturing times during a turning motion of the imaging means or of the movable device on which the imaging means is mounted.

15. The method according to claim 1, wherein
the method for determining a static element is started when a turning movement of the imaging means or of the movable device is determined.

16. The method according to claim 1, wherein
the method comprises a step of determining underexposed or overexposed areas in the first image and the second image,
wherein the underexposed or overexposed areas in the first image and the second image are excluded from determining static elements.

17. The method according to claim 1, wherein
when a number of determined static elements exceeds a third threshold, the output signal is generated.

18. The method according to claim 17, wherein
the output signal initiates performing a lens-cleaning procedure or reporting to a user of a determined imaging means state or stopping moving the movable device on which the imaging means is mounted or moving the movable device on which the imaging means is mounted to a cleaning position.

19. An image processing system configured to perform the method according to claim 1.

20. An imaging device comprising the image processing system according to claim 19.

21. A movable device equipped with an imaging device according to claim 20, wherein
the movable device is one of an automobile device, an autonomous movable device, an autonomous lawn mower, a land vehicle, a car, a motorcycle, an aerial vehicle, a sea vehicle, an orbital vehicle, a spacecraft.

22. A computer program product, the computer program product comprising a non-transitory computer readable medium for performing the method according to claim 1 when executed on a computer or signal processor.

* * * * *